United States Patent [19]

Buzzetti et al.

[11] Patent Number: 5,576,330

[45] Date of Patent: Nov. 19, 1996

[54] BIOLOGICALLY ACTIVE 3-SUBSTITUTED OXINDOLE DERIVATIVES USEFUL AS ANTI-ANGIOGENIC AGENTS

[75] Inventors: Franco Buzzetti, Monza; Antonio Longo, Milan; Maria G. Brasca, Cusago; Fabrizio Orzi, Milan; Angelo Crugnola, Varese; Dario Ballinari, S. Donato Mil.; Mariangela Mariani, Desio, all of Italy

[73] Assignee: Farmitalia Carlo Erba S.r.l., Milan, Italy

[21] Appl. No.: 354,215

[22] Filed: Dec. 12, 1994

[30] Foreign Application Priority Data

Dec. 22, 1993 [GB] United Kingdom .................. 9326136

[51] Int. Cl.$^6$ .......................... A61K 31/47; A61K 31/40; A61K 31/015
[52] U.S. Cl. .......................... 514/307; 514/311; 514/418; 514/765; 514/825; 514/863; 514/866; 514/886; 514/908
[58] Field of Search .................................. 514/418, 307, 514/311, 765, 886, 866, 863, 825, 908

[56] References Cited

U.S. PATENT DOCUMENTS

| 5,122,537 | 6/1992 | Buzzetti et al. | 514/510 |
|---|---|---|---|
| 5,130,472 | 7/1992 | Buzzetti et al. | 560/252 |
| 5,374,652 | 12/1994 | Buzzetti et al. | 514/418 |

FOREIGN PATENT DOCUMENTS

| WO91/13055 | 9/1991 | WIPO . |
|---|---|---|
| WO92/21660 | 12/1992 | WIPO . |
| WO93/01182 | 1/1993 | WIPO . |
| WO94/03427 | 2/1994 | WIPO . |
| WO94/14808 | 7/1994 | WIPO . |

OTHER PUBLICATIONS

R. Montesano, et al., Tumor–Promoting Phorbol Esters Induce Angiogenesis In Vitro, Cell, 42:469–477. 1985.
S. Taylor, et al., Protamine is an Inhibitor of Angiogenesis, Nature 297:307–312. May 27, 1982.
W. Herblin, et al., "Recent Advances in Angiogenesis Inhibitors", Oncologic, Endocrine & Metabolic, Ashely Pub., pp. 642–653. 1994.
T. Oikawa, Strategies to Find Novel Angiogenesis Inhibitors as Potentiao Therapeutic Agents for Cancer, Cur. Med. Chem. 1:406–417. 1995.
H. Terano, et al., Angiogenesis Inhibitors of Microbial Origin, Drug of the Future 18(3):239–245. 1993.
C. Baillie, et al., Tumour Vasculature—A Potential Therapeutic Target, Brit. J. Can., 72:257–267. 1995.

*Primary Examiner*—John W. Rollins
*Attorney, Agent, or Firm*—Oblon, Spivak, McClelland, Maier & Neustadt, P.C.

[57] ABSTRACT

The new use of a compound of formula (I)

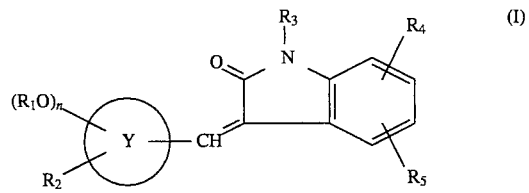

wherein
  Y is a bicyclic ring selected from naphthalene, tetralin, quinoline, isoquinoline and indole;
  n is zero or an integer of 1 to 3;
  $R_1$ is hydrogen, $C_1$–$C_6$ alkyl or $C_2$–$C_6$ alkanoyl;
  $R_2$ is hydrogen, halogen, $C_1$–$C_6$ alkyl, cyano, carboxy, nitro, or NHR, wherein R is hydrogen or $C_1$–$C_6$ alkyl;
  $R_3$ is hydrogen or $C_1$–$C_6$ alkyl;
  $R_4$ is hydrogen, hydroxy, $C_1$–$C_6$ alkoxy, $C_2$–$C_6$ alkanoyloxy, carboxy, nitro or NHR, wherein R is as defined above;
  $R_5$ is hydrogen, $C_1$–$C_6$ alkyl or halogen; or a pharmaceutically acceptable salt thereof;
and wherein when Y is naphthalene then n is zero or an integer of 1 to 3, whereas when Y is tetralin, quinoline, isoquinoline or indole then n is zero, 1 or 2; and wherein when the bicyclic ring Y is naphthalene, quinoline, isoquinoline or indole, then each of the substituents $OR_1$, $R_2$ and oxindolylidene may be independently on either of the aryl or heteroaryl moieties of said bicyclic ring, whereas only the benzene moiety is substituted when Y is tetralin;
and wherein when Y is naphthalene, tetralin, quinoline or isoquinoline, then $R_2$ is hydrogen, halogen, cyano or $C_1$–$C_6$ alkyl and $R_3$, $R_4$ and $R_5$ are hydrogen; whereas when Y is indole, then $R_2$ is hydrogen, halogen, $C_1$–$C_6$ alkyl, cyano, carboxy, nitro or —NHR, in which R is as defined above, $R_3$ is hydrogen or $C_1$–$C_6$ alkyl, $R_4$ is hydrogen, hydroxy, $C_1$–$C_6$ alkoxy, $C_1$–$C_6$ alkanoyloxy, carboxy, nitro or —NHR, wherein R is as defined above, and $R_5$ is hydrogen, halogen or $C_1$–$C_6$ alkyl;
as anti-angiogenic agent is disclosed.

22 Claims, No Drawings

BIOLOGICALLY ACTIVE 3-SUBSTITUTED OXINDOLE DERIVATIVES USEFUL AS ANTI-ANGIOGENIC AGENTS

The present invention relates to the use of 3-substituted oxindole derivatives as angiogenesis inhibitors.

As known, angiogenesis, i.e. the growth of new blood vessels, is an essential component in the development of several pathological conditions in mammals, for instance chronic inflammation, diabetic retinopathy, psoriasis, rheumatoid arthritis, solid tumor growth and development of metastases.

Accordingly, there is a need in therapy for drugs able to suppress the growth of new blood vessels. WO 91/13055 and WO 93/01182 provide in their complex aryl- and heteroaryl-methylene derivatives having tyrosine kinase inhibition activity.

Accordingly, these prior art compounds can be useful in the treatment of cancer and other pathological proliferative conditions, typically in inhibiting the development of the atheromatous plaque in mammals. Now we have found that a selected class of known compounds according to WO 91/13055 and WO 93/01182 are active as angiogenesis inhibitors.

Accordingly, the present invention relates to the use of a compound of formula (I)

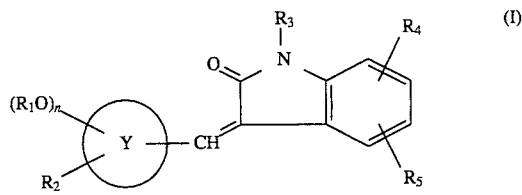

wherein
Y is a bicyclic ring selected from naphthalene, tetralin, quinoline, isoquinoline and indole;
n is zero or an integer of 1 to 3;
$R_1$ is hydrogen, $C_1$–$C_6$ alkyl or $C_2$–$C_6$ alkanoyl;
$R_2$ is hydrogen, halogen, $C_1$–$C_6$ alkyl, cyano, carboxy, nitro, or NHR, wherein R is hydrogen or $C_1$–$C_6$ alkyl;
$R_3$ is hydrogen or $C_1$–$C_6$ alkyl;
$R_4$ is hydrogen, hydroxy, $C_1$–$C_6$ alkoxy, $C_2$–$C_6$ alkanoyloxy, carboxy, nitro or NHR, wherein R is as defined above;
$R_5$ is hydrogen, $C_1$–$C_6$ alkyl or halogen; or a pharmaceutically acceptable salt thereof;
and wherein when Y is naphthalene then n is zero or an integer of 1 to 3, whereas when Y is tetralin, quinoline, isoquinoline or indole then n is zero, 1 or 2;
and wherein when the bicyclic ring Y is naphthalene, quinoline, isoquinoline or indole then each of the substituents $OR_1$, $R_2$ and oxindolylidene may be independently on either of the aryl or heteroaryl moieties of said bicyclic ring, whereas only the benzene moiety is substituted when Y is tetralin;
and wherein when Y is naphthalene, tetralin, quinoline or isoquinoline, then $R_2$ is hydrogen, halogen, cyano or $C_1$–$C_6$ alkyl and $R_3$, $R_4$ and $R_5$ are hydrogen; whereas when Y is indole, then $R_2$ is hydrogen, halogen, $C_1$–$C_6$ alkyl, cyano, carboxy, nitro or —NHR in which R is as defined above, $R_3$ is hydrogen or $C_1$–$C_6$ alkyl, $R_4$ is hydrogen, hydroxy, $C_1$–$C_6$ alkoxy, $C_2$–$C_6$ alkanoyloxy, carboxy, nitro or —NHR wherein R is as defined above, and $R_5$ is hydrogen, halogen or $C_1$–$C_6$ alkyl; in the preparation of a medicament for use as anti-angiogenic agent.

The present invention also provides a compound of formula (I), as defined above, or a pharmaceutically acceptable salt thereof, for use in the inhibition of angiogenesis in mammals, including humans.

Object of the present invention is also to provide a pharmaceutical composition having anti-angiogenetic activity comprising a pharmaceutically acceptable carrier and/or diluent and, as an active principle, a compound of formula (I), as defined above, or a pharmaceutically acceptable salt thereof.

The term tetralin is meant to refer to a 5,6,7,8-tetrahydronaphthalene ring.

The oxidolylidene substituent is preferably linked to position 1 or 2 of the naphthalene or tetralin ring, to position 4 or 5 of the quinoline ring, to position 5 or 8 of the isoquinoline ring and to position 2 or 3 of the indole ring, in particular to position 3.

The $R_2$ substituent is preferably on the benzene moiety when Y is indole.

The $OR_1$ groups and the oxindolylidene radical are preferably on the same benzene moiety when Y is naphthalene.

The $OR_1$ groups are preferably on the benzene moiety of the quinoline, isoquinoline or indole ring, whereas the oxindolylidene radical may be independently on either of the aryl or heteroaryl moiety of said bicyclic ring system.

When n is 2 or 3, the OR groups may be the same or different.

An $OR_1$ substituent is preferably linked to position 2, 3 or 4 when Y is 1-tetralyl or 1-naphthyl; it is preferably linked to position 1, 3 or 4 when Y is 2-tetralyl or 2-naphthyl. An $OR_1$ substituent is preferably linked to position 6, 7 or 8 when Y is 4- or 5-quinolyl. An $OR_1$ substituent is preferably linked to position 4, 5, 6 or 7 when Y is 2- or 3-indolyl, in particular to position 5.

Of course only one of the substituents $OR_1$, $R_2$ and oxindolylidene can be linked to the same position in the bicyclic ring system Y.

The $R_4$ substituent is preferably linked to position 4 or 5, in particular to position 5.

When Y is indole and $R_4$ is carboxy, nitro or NHR, in which R is as defined above, the $R_2$ substituent preferably has not the same meanings. Vice versa, when $R_2$ is carboxy, nitro or NHR, in which R is as defined above, the $R_4$ substituent preferably is other than carboxy, nitro or NHR.

The alkyl groups, and the alkyl moiety in the alkanoyl groups, may be branched or straight alkyl chains. A $C_1$–$C_6$ alkyl group is preferably a $C_1$–$C_4$ alkyl group, e.g. methyl, ethyl, propyl, isopropyl, butyl, sec-butyl or tert-butyl, in particular methyl or ethyl.

A $C_2$–$C_6$ alkanoyl group is preferably a $C_2$–$C_4$ alkanoyl group, in particular acetyl, propionyl or butyryl.

A halogen is preferably chlorine, bromine or fluorine, in particular fluorine.

The invention also includes within its scope all the possible isomers, stereoisomers, in particular Z- and E-isomers and their mixtures, and the metabolites and the metabolic precursors or bio-precursors (otherwise known as pro-drugs) of the compounds of formula (I).

As already said, the invention includes within its scope also the pharmaceutically acceptable salts of the compounds of formula (I).

Pharmaceutically acceptable salts of the compounds of the invention include acid addition salts, with inorganic, e.g. nitric, hydrochloric, hydrobromic, sulphuric, perchloric and phosphoric acids, or organic, e.g. acetic, propionic, glycolic, lactic, oxalic, malonic, malic, maleic, tartaric, citric, benzoic, cinnamic, mandelic and salicylic acids, and salts with inorganic, e.g. alkali metal, especially sodium or potassium, bases or alkaline-earth metal, especially calcium or magnesium bases, or with organic bases, e.g. alkylamines, preferably triethyl-amine.

As stated above, the present invention also includes within its scope pharmaceutically acceptable bio-precursors (otherwise known as pro-drugs) of the compounds of formula (I), i.e. compounds which have a different formula to formula (I) above, but which nevertheless upon administration to a human being are converted directly or indirectly in vivo into a compound of formula (I).

Preferred compounds of formula (I) are those wherein, subject to the above proviso, Y is naphthalene, tetralin, quinoline or indole and wherein when Y is naphthalene, tetralin or quinoline, then n is zero, 1 or 2; and $R_1$, $R_2$, $R_3$, $R_4$ and $R_5$ are hydrogen; whereas when Y is indole, then n is zero or 1;

$R_1$ is hydrogen or $C_1$–$C_4$ alkyl;

$R_2$ is hydrogen, amino, carboxy, cyano or $C_1$–$C_4$ alkyl;

$R_3$ and $R_5$ are hydrogen; and the pharmaceutically acceptable salts thereof.

Examples of specific preferred componds of formula (I) are:

3-[(2'-naphthyl)methylen]-2-oxindole m.p.: 207°–209° IR: 3300–3100 (NH), 1720 (CO), 1630,1620 cm$^{-1}$;

3-[(1'-hydroxy-2'-naphthyl)methylen]-2-oxindole IR: 3500–3100 (OH, NH), 1680 (CO) cm$^{-1}$;

3-[(3'-hydroxy-2'-naphthyl)methylen]-2-oxindole;

3-[(4'-hydroxy-2'-naphthyl)methylen]-2-oxindole;

3-[(1'-naphthyl)methylen]-2-oxindole m.p.: 179°–81° IR: 3500–3100 (OH, NH), 1680 (CO), 1610,1560 cm$^{-1}$;

3-[(2'-hydroxy-1'-naphthyl)methylen]-2-oxindole;

3-[(3'-hydroxy-1'-naphthyl)methylen]-2-oxindole;

3-[(4'-hydroxy-1'-naphthyl)methylen]-2-oxindole IR: 3500–3100 (NH,OH), 1680 (CO), 1610,1570,1510 cm$^{-1}$;

3-[(3'-hydroxy-1'-tetralyl)methylen]-2-oxindole;

3-[(4'-hydroxy-1'-tetralyl)methylen]-2-oxindole;

3-[(2'-hydroxy-1'-tetralyl)methylen]-2-oxindole;

3-[(1'-tetralyl)methylen]-2-oxindole;

3-[(2'-tetralyl)methylen]-2-oxindole;

3-[(1'-hydroxy-2'-tetralyl)methylen]-2-oxindole;

3-[(3'-hydroxy-2'-tetralyl)methylen]-2-oxindole IR: 3500–3100 (NH,OH), 1685 (CO), 1610,1570 (C=C)cm$^{-1}$;

3-[(4'-hydroxy-2'-tetralyl)methylen]-2-oxindole;

3-[(1',4'-dihydroxy-2'-tetralyl)methylen]-2-oxindole IR: 3500–3100 (OH,NH), 1680 (CO), 1620 cm$^{-1}$; 3[(2-quinolyl)methylen]-2-oxindole IR: 3180 (NH), 1710 (CO), 1620,1595,1505 (C=C) cm$^{-1}$; 3[(4-hydroxy-2-quinolyl)methylen]-2-oxindole; 3[(3-quinolyl)methylen]-2-oxindole IR: 3500–3100 (NH), 1695 (CO), 1620,1580 (C=C,C=N); 3[(4-quinolyl)methylen]-2-oxindole m.p.: 277°–9° IR: 3300–2600 (NH), 1710 (CO), 1640,1620,1570 cm$^{-1}$; 3[(5-quinolyl) methylen]-2-oxindole; 3[(6-hydroxy-5-quinolyl)methylen]-2-oxindole; 3[(7-hydroxy-5-quinolyl)methylen]-2-oxindole; 3[(8-hydroxy-5-quinolyl)methylen]-2-oxindole m.p.: 282°–4° IR: 3400–2800 (NH,OH), 1690 (CO), 1670,1610 (C=C)cm$^{-1}$; 3[(6-quinolyl)methylen]-2-oxindole; 3[(5-hydroxy-6-quinolyl)methylen]-2-oxindole; 3[(7-hydroxy-6-quinolyl)methylen]-2-oxindole; 3[(8-hydroxy-6-quinolyl)methylen]-2-oxindole; 5-(hydroxy-3[(3'-indolyl)methylen]-2-oxindole IR: 3600–2500 (NH,OH), 1650 (CO) , 1600,1580 cm$^{-1}$; 3[(5'-carboxy-3'-indolyl)methylen]-2-oxindole IR: 3600–2100 (NH,OH), 1710 (CO), 1640,1620,1600 (atom); 3[(5'-amino-3'-indolyl)methylen]-2-oxindole IR: 3300,2380 (NH), 1670 (CO), 1600,1510 (C=C); 5-carboxy-3[(3'-indolyl)methylen]-2-oxindole; 5-amino-3[(3'-indolyl)methylen]-2-oxindole; 5-hydroxy-3 [(5'-hydroxy-3'-indolyl)methylen]-2-oxindole IR: 3600–2600 (NH,OH), 1655 (CO), 1605,1585 (C=C); 5-hydroxy-3-[(7'-hydroxy-3'-indolyl)methylen]-2-oxindole; 3[(5',7'-dihydroxy-3'-indolyl)methylen]-2-oxindole; 5-amino-3[(5'-hydroxy-3'-indolyl)methylen]-2-oxindole; 5-hydroxy-3[(5'-amino-3'-indolyl)methylen]-2-oxindole; 5-carboxy-3[(5'-hydroxy-3'-indolyl)methylen]-2-oxindole; 5-hydroxy-3[(5'-carboxy-3'-indolyl)methylen]-2-oxindole; 5-amino-3[(7'-hydroxy-3'-indolyl)methylen]-2-oxindole; 5-carboxy-3[(7'-hydroxy-3'-indolyl)methylen]-2-oxindole; 5-methoxy-3[(5'-methoxy-3'-indolyl)methylen]-2-oxindole; 5-acetoxy-3[(5'-acetoxy-3'-indolyl)methylen]-2-oxindole; 3[(5'-carboxy-3'-indolyl)methylen]-2-oxindole; 3[(5'-amino-3'-indolyl)methylen]-2-oxindole; 3[(5'-nitro-3'-indolyl)methylen]-2-oxindole; 3[(1'-methyl-3'-indolyl)methylen]-2-oxindole; 3[(3'-indolyl)methylen]-1-methyl-2-oxindole m.p.: 230° IR: 3300–2000 (NH), 1680 (CO), 1610,1600,1570 (C=C);

if the case, either as single Z- or E- diastereoisomers or as a mixture thereof; and the pharmaceutically acceptable salts thereof.

The compounds of formula (I) according to the present invention, and the salts thereof, are known compounds and can be prepared by a process comprising reacting a compound of formula (II)

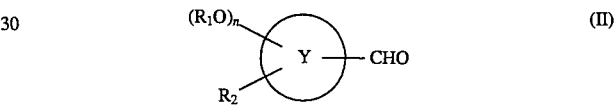

wherein Y, $R_1$, $R_2$ and n are as defined above, with a compound of formula (III)

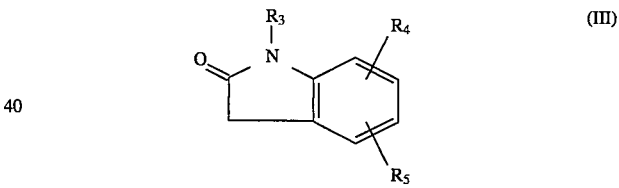

wherein $R_3$, $R_4$ and $R_5$ are as defined above, using the methods and conditions as disclosed in the aforesaid international patent applications WO. 91/13055 and WO. 93/01182.

The compounds of formulae (II) and (III) are known or may be obtained as described in the aforesaid patent applications.

PHARMACOLOGY

The compounds of the invention have been found to be active as angiogenesis inhibitors.

An angiogenesis inhibitor is an agent capable of suppressing the growth of new blood vessels. Therefore, the compounds of the present invention are useful in treating several pathological conditions in mammals, including humans, where the growth of new blod vessels is detrimental, for example in chronic inflammation, diabetic retinopathy, psoriasis, rheumatoid arthritis, tumor growth, in particular solid tumors, and development of metastases.

In particular, in cancer therapy the compounds of the invention can be administered alone or in association with an antitumor agent as herebelow defined.

The angiogenesis inhibitor activity of the compounds of the present invention is shown, e.g., by the fact that they have been found to be active in the chorioallantoic membrane (CAM) test according to the Folkman's method [Nature. 297, 307 (1982)].

For instance, the representative compound of the invention 3-[(1',4'-dihydroxy-2'-tetralyl)methylen]-2-oxindole, internal code FCE 26806, when thested in the CAM assay provided 87% positive CAMs, with inhibition area at 40 μmol/pellet.

In addition, FCE 26806 was found to be active in the collagen gel assay as described by R. Montesano et al. in Cell 42, 469 (1985), inhibiting the invasion of the endothelial cells in a dose-dependent manner (43% and 22% inhibition at the concentration of 20 and 10 μM, respectively).

The compounds of the invention can be administered in a variety of dosage forms, e.g. orally, in the form of tablets, capsules, sugar or film-coated tablets, liquid solutions or suspensions; rectally, in the form of suppositories; parenterally, e.g. intramuscularly, or by intravenous injection or infusion; or topically.

The dosage depends on the age, weight, condition of the patient and administration route; for example, the dosage adopted for oral administration of the compound 3-[(1,4-dihydroxy-2'-tetralyl)methylen]-2-oxindole to adult humans may range from about 5 to about 150–200 mg per dose, from 1 to 5 times daily. Of course, these dosage regimens may be adjusted to provide the optimal therapeutic response.

The pharmaceutical compositions according to the invention are usually prepared following conventional methods and are administered in a pharmaceutically suitable form.

For example, the solid oral forms may contain, together with the active compound, diluents, e.g., lactose, dextrose, saccharose, cellulose, corn starch or potato starch; lubricants, e.g., silica, talc, stearic acid, magnesium or calcium stearate, and/or polyethylene glycols; binding agents, e.g., starches, arabic gums, gelatin, methylcellulose, carboxymethylcellulose or polyvinyl pyrrolidone; disaggregating agents, e.g. a starch, alginic acid, alginates or sodium starch glycolate, effervescing mixtures; dyestuffs; sweeteners; wetting agents, such as lecithin, polysorbates, laurylsulphates; and, in general, non-toxic and pharmacologically inactive substances used in pharmaceutical formulations. Said pharmaceutical preparations may be manufactured in known manner, for example, by means of mixing, granulating, tabletting, sugar-coating or film-coating processes.

The liquid dispersion for oral administration may be, e.g., syrups, emulsions and suspensions.

The syrup may contain as carrier, for example, saccharose or saccharose with glycerine and/or mannitol and/or sorbitol.

The suspensions and the emulsions may contain as carrier, for example, a natural gum, agar, sodium alginate, pectin, methylcellulose, carboxymethylcellulose or polyvinyl alcohol.

The suspensions or solutions for intramuscular injections may contain, together with the active compound, a pharmaceutically acceptable carrier, e.g. sterile water, olive oil, ethyl oleate, glycols, e.g. propylene glycol, and, if desired, a suitable amount of lidocaine hydrochloride.

The solutions for intravenous injections or infusions may contain as carrier, for example, sterile water or, preferably, they may be in the form of sterile, aqueous, isotonic saline solutions.

The suppositories may contain, together with the active compound, a pharmaceutically acceptable carrier, e.g. cocoa-butter, polyethylene glycol, a polyoxyethylene sorbitan fatty acid ester surfactant or lecithin.

Compositions for topical application, e.g., creams, lotions, or pastes, can be prepared by mixing the active ingredient with a conventional oleaginous or emulsifying excipient.

A further object of the present invention is a combined method of treatment of the above mentioned pathological conditions in mammals, including humans, in need of such treatment, said method comprising administering 1) an angiogenesis inhibitor according to the invention, or a pharmaceutically acceptable salt thereof, and 2) a different pharmaceutically active agent, typically an antitumor agent, in amounts and close enough together in time sufficient to produce a therapeutically useful effect.

The present invention also provides products containing an angiogenesis inhibitor of the invention, or a pharmaceutically acceptable salt thereof, and an antitumor agent as a combined preparation for simultaneous, separate or sequential use in anti-cancer therapy.

The term "antitumor agent" is meant to comprise both a single antitumor drug and "cocktails", i.e. a mixture of such drugs, according to clinical practice.

Examples of antitumor agents that can be formulated with an angiogenesis inhibitor according to the invention or alternatively, can be administered in a combined method of treatment, include doxorubicin, daunomycin, epirubicin, idarubicin, etoposide, fluorouracil, mephalan, cyclophosphamide, bleomycin, vinblastine and mitomycin and mixtures of two or more thereof.

The angiogenesis inhibitors of the invention can therefore be used in a treatment to ameliorate a cancer. They may be administered to a patient suffering from a cancer treatable with an antitumor agent, for example an anthracycline glycoside such as doxorubicin, daunomycin, epirubicin or idarubicin as mentioned above, together with the antitumor agent.

An angiogenesis inhibitor of the invention alone or in association with an antitumor agent such as an anthracycline glycoside can be therefore administered to improve the condition of a patient having a leukaemia such as myeloblastic leukaemia, lymphoma, sarcoma, neuroblastoma, Wilm's tumor or malignant neoplasm of the bladder, breast, lung or thyroid.

The following examples of pharmaceutical formulations illustrate but do not limit the present invention.

EXAMPLE 1

Tablets each weighing 0.150 g and containing 25 mg of the active substance, can be manufactured as follows:

composition (for 10,000 tablets):

| | |
|---|---|
| 3-[(3'-hydroxy-2'-tetralyl)methylen]-2-oxindole | 250 g |
| Lactose | 800 g |
| Corn starch | 415 g |
| Talc powder | 30 g |
| Magnesium stearate | 5 g |

The 3-[(3'-hydroxy-2'-tetralyl)methylen]-2-oxindole, the lactose and half the corn starch are mixed; the mixture is then forced through a sieve of 0.5 mm mesh size. Corn starch (10 g) is suspended in warm water (90 ml) and the resulting paste is used to granulate the powder. The granulate is dried, comminuted on a sieve of 1.4 mm mesh size, then the remaining quantity of starch, talc and magnesium stearate are added, carefully mixed and processed into tablets.

EXAMPLE 2

Capsules, each dosed at 0.200 g and containing 20 mg of the active substance can be prepared.

Composition for 500 capsules:

| | |
|---|---|
| 3-[(1',4'-dihydroxy-2'-tetralyl)methylen]-2-oxindole | 10 g |
| Lactose | 80 g |
| Corn starch | 5 g |
| Magnesium stearate | 5 g |

This formulation is encapsulated in two-piece hard gelatin capsules and dosed at 0.200 g for each capsule.

We claim:

1. A composition comprising
(a) a therapeutically effective amount an angiogenesis inhibitor of the formula (I):

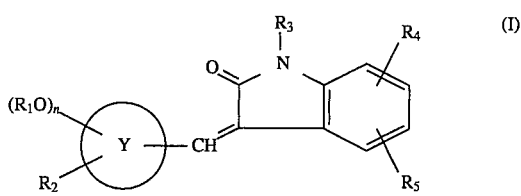

or a pharmaceutically acceptable salt thereof, wherein

Y is a bicyclic ring selected from naphthalene, tetralin, quinoline, isoquinoline and indole;

n is zero or an integer of 1 to 3;

$R_1$ is hydrogen, $C_1$–$C_6$ alkyl or $C_1$–$C_6$ alkanoyl;

$R_2$ is hydrogen, halogen, $C_1$–$C_6$ alkyl, cyano, carboxy, nitro or NHR, wherein R is hydrogen or $C_1$–$C_6$ alkyl;

$R_3$ is hydrogen or $C_1$–$C_6$ alkyl;

$R_4$ is hydrogen, hydroxy, $C_1$–$C_6$ alkoxy, $C_2$–$C_6$ alkanoyloxy, carboxy, nitro or NHR, wherein R is as defined above; and $R_5$ is hydrogen, $C_1$–$C_6$ alkyl or halogen;

wherein when Y is tetralin, quinoline, isoquinoline or indole then n is zero, 1 or 2; when Y is naphthalene, quinoline, isoquinoline or indole, then each of the substituents $OR_1$, $R_2$ and oxindolylidene may be independently on either of the aryl or heteroaryl moieties of Y, whereas only the benzene moiety is substituted when Y is tetralin; and when Y is naphthalene, tetralin, quinoline or isoquinoline, then $R_2$ is hydrogen, halogen, cyano or $C_1$–$C_6$ alkyl and $R_3$, $R_4$ and $R_5$ are hydrogen; whereas when Y is indole, then $R_2$ is hydrogen, halogen, $C_1$–$C_6$ alkyl, cyano, carboxy, nitro or —NHR, in which R is as defined above, $R_3$ is hydrogen or $C_1$–$C_6$ alkyl, $R_4$ is hydrogen, hydroxy, $C_1$–$C_6$ alkoxy, $C_2$–$C_6$ alkanoyloxy, carboxy, nitro or —NHR, wherein R is as defined above, and $R_5$ is hydrogen, halogen or $C_1$–$C_6$ alkyl; and (b) an effective amount of an antitumor agent.

2. A method of inhibiting angiogenesis, comprising administering to a host in need thereof a therapeutically effective amount of a compound of formula (I)

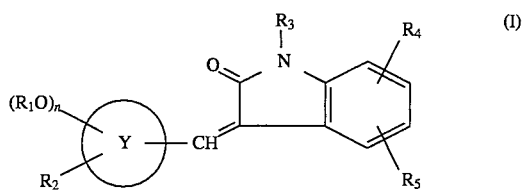

wherein

Y is a bicyclic ring selected from naphthalene, tetralin, quinoline, isoquinoline and indole;

n is zero or an integer of 1 to 3;

$R_1$ is hydrogen, $C_1$–$C_6$ alkyl or $C_2$–$C_6$ alkanoyl;

$R_2$ is hydrogen, halogen, $C_1$–$C_6$ alkyl, cyano, carboxy, nitro, or NHR, wherein R is hydrogen or $C_1$–$C_6$ alkyl;

$R_3$ is hydrogen or $C_1$–$C_6$ alkyl;

$R_4$ is hydrogen, hydroxy, $C_1$–$C_6$ alkoxy, $C_2$–$C_6$ alkanoyloxy, carboxy, nitro or NHR, wherein R is as defined above;

$R_5$ is hydrogen, $C_1$–$C_6$ alkyl or halogen; or a pharmaceutically acceptable salt thereof;

and wherein when Y is naphthalene then n is zero or an integer of 1 to 3, whereas when Y is tetralin, quinoline, isoquinoline or indole then n is zero, 1 or 2; and wherein when the bicyclic ring Y is naphthalene, quinoline, isoquinoline or indole, then each of the substituents $OR_1$, $R_2$ and oxindolylidene may be independently on either of the aryl or heteroaryl moieties of said bicyclic ring, whereas only the benzene moiety is substituted when Y is tetralin;

and wherein when Y is naphthalene, tetralin, quinoline or isoquinoline, then $R_2$ is hydrogen, halogen, cyano or $C_1$–$C_6$ alkyl and $R_3$, $R_4$ and $R_5$ are hydrogen; whereas when Y is indole, then $R_2$ is hydrogen, halogen, $C_1$–$C_6$ alkyl, cyano, carboxy, nitro or —NHR, in which R is as defined above, $R_3$ is hydrogen or $C_1$–$C_6$ alkyl, $R_4$ is hydrogen, hydroxy, $C_1$–$C_6$ alkoxy, $C_2$–$C_6$ alkanoyloxy, carboxy, nitro or —NHR, wherein R is as defined above, and $R_5$ is hydrogen, halogen or $C_1$–$C_6$ alkyl.

3. A method, according to claim 2, wherein in said compound

Y is naphthalene, tetralin, quinoline or indole, and wherein when

Y is naphthalene, tetralin or quinoline, then n is zero 1 or 2; and $R_1$, $R_2$, $R_3$, $R_4$ and $R_5$ are hydrogen; whereas when Y is indole, then n is zero or 1;

$R_1$ is hydrogen or $C_1$–$C_4$ alkyl;

$R_2$ is hydrogen, amino, carboxy, cyano or $C_1$–$C_4$ alkyl; and $R_3$ and $R_5$ are hydrogen.

4. A method according to claim 2 wherein said compound is chosen from

3-[(2'-naphthyl)methylen]-2-oxindole;
3-[(1'-hydroxy-2'-naphthyl)methylen]-2-oxindole;
3-[(3'-hydroxy-2'-naphthyl)methylen]-2-oxindole;
3-[(4'-hydroxy-2'-naphthyl)methylen]-2-oxindole;
3-[(1'-naphthyl)methylen]-2-oxindole;
3-[(2'-hydroxy-1'-naphthyl)methylen]-2-oxindole;
3-[(3'-hydroxy-1'-naphthyl)methylen]-2-oxindole;
3-[(4'-hydroxy-1'-naphthyl)methylen]-2-oxindole;
3-[(3'-hydroxy-1'-tetralyl)methylen]-2-oxindole;

3-[(4'-hydroxy-1'-tetralyl)methylen]-2-oxindole;
3-[(2'-hydroxy-1'-tetralyl)methylen]-2-oxindole;
3-[(1'-tetralyl)methylen]-2-oxindole;
3-[(2'-tetralyl)methylen]-2-oxindole;
3-[(1'-hydroxy-2'-tetralyl)methylen]-2-oxindole;
3-[(3'-hydroxy-2'-tetralyl)methylen]-2-oxindole;
3-[(4'-hydroxy-2'-tetralyl)methylen]-2-oxindole;
3-[(1',4'-dihydroxy-2'-tetralyl)methylen]-2-oxindole;
3-[(2-quinolyl)methylen]-2-oxindole;
3-[(4-hydroxy-2-quinolyl)methylen]-2-oxindole;
3-[(3-quinolyl)methylen]-2-oxindole;
3-[(4-quinolyl)methylen]-2-oxindole;
3-[(5-quinolyl)methylen]-2-oxindole;
3-[(6-hydroxy-5-quinolyl)methylen]-2-oxindole;
3-[(7-hydroxy-5-quinolyl)methylen]-2-oxindole;
3-[(8-hydroxy-5-quinolyl)methylen]-2-oxindole;
3-[(6-quinolyl) methylen]-2-oxindole;
3-[(5-hydroxy-6-quinolyl)methylen]-2-oxindole;
3-[(7-hydroxy-6-quinolyl)methylen]-2-oxindole;
3-[(8-hydroxy-6-quinolyl) methylen]-2-oxindole;
5-hydroxy-3-[(3'-indolyl)methylen]-2-oxindole;
3-[(5'-carboxy-3'-indolyl)methylen]-2-oxindole;
3-[(5'-amino-3'-indolyl)methylen]-2-oxindole;
5-carboxy-3-[(3'-indolyl)methylen]-2-oxindole;
5-amino-3-[(3'-indolyl)methylen]-2-oxindole;
5-hydroxy-3-[(5'-hydroxy-3'-indolyl)methylen]-2-oxindole;
5-hydroxy-3-[(7'-hydroxy-3'-indolyl)methylen]-2-oxindole;
3-[(5',7'-dihydroxy-3'-indolyl)methylen]-2-oxindole;
5-amino-3-[(5'-hydroxy-3'-indolyl)methylen]-2-oxindole;
5-hydroxy-3-[(5'-amino-3'-indolyl)methylen]-2-oxindole;
5-carboxy-3-[(5'-hydroxy-3'-indolyl)methylen]-2-oxindole;
5-hydroxy-3-[(5'-carboxy-3'-indolyl)methylen]-2-oxindole;
5-amino-3-[(7'-hydroxy-3'-indolyl)methylen]-2oxindole;
5-carboxy-3-[(7'-hydroxy-3'-indolyl)methylen]-2-oxindole;
5-methoxy-3-[(5'-methoxy-3'-indolyl)methylen]-2-oxindole;
5-acetoxy-3-[(5'-acetoxy-3'-indolyl)methylen]-2-oxindole;
3-[(5'-carboxy-3'-indolyl)methylen]-2-oxindole;
3-[(5'-amino-3'-indolyl)methylen]-2-oxindole;
3-[(5'-nitro-3'-indolyl)methylen]-2-oxindole;
3-[(1'-methyl-3'-indolyl)methylen]-2-oxindole;
3-[(3'-indolyl)methylen]-1-methyl-2-oxindole;
if the case, either as single Z- or E-diastereoisomers or as a mixture thereof; or a pharmaceutically acceptable salt thereof.

5. A method for improving the conditions of a patient having leukemia, lymphoma, sarcoma, neuroblastoma, Wilm's tumor or a malignant neoplasm of the bladder, breast, lung or thyroid, said method comprising administering to said patient an effective amount of a compound of formula (I), as defined in claim 2, or a pharmaceutically acceptable salt thereof, alone or in association with an antitumor agent.

6. The method of claim 5, wherein said administering further comprises administering said antitumor agent.

7. The method of claim 5, wherein said compound is administered to a host in need of treatment for leukemia.

8. The method of claim 5, wherein said compound is administered to a host in need of treatment for lymphoma.

9. The method of claim 5, wherein said compound is administered to a host in need of treatment for sarcoma.

10. The method of claim 5, wherein said compound is administered to a host in need of treatment for neuroblastoma.

11. The method of claim 5, wherein said compound is administered to a host in need of treatment for Wilm's tumor.

12. The method of claim 5, wherein said compound is administered to a host in need of treatment for a malignant neoplasm of the bladder.

13. The method of claim 5, wherein said compound is administered to a host in need of treatment for a malignant neoplasm of the breast.

14. The method of claim 5, wherein said compound is administered to a host in need of treatment for a malignant neoplasm of the lung.

15. The method of claim 5, wherein said compound is administered to a host in need of treatment for a malignant neoplasm of the thyroid.

16. The method of claim 2, wherein said compound is administered to a host in need of treatment for chronic inflammation.

17. The method of claim 2, wherein said compound is administered to a host in need of treatment for diabetic retinopathy.

18. The method of claim 2, wherein said compound is administered to a host in need of treatment for psoriasis.

19. The method of claim 2, wherein said compound is administered to a host in need of treatment for rheumatoid arthritis.

20. The method of claim 2, wherein said compound is administered to a host having a solid tumor.

21. The method of claim 2, wherein said compound is administered to a host in need of prevention of development of metastases.

22. A kit for the treatment of cancer, comprising:
(a) an effective amount of an angiogenesis inhibitor of the formula (I):

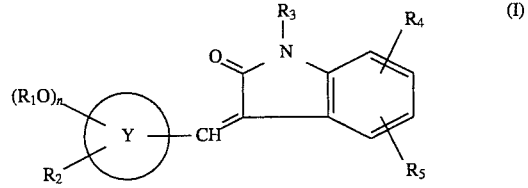

or a pharmaceutically acceptable salt thereof, wherein

Y is a bicyclic ring selected from naphthalene, tetralin, quinoline, isoquinoline and indole;

n is zero or an integer of 1 to 3;

$R_1$ is hydrogen, $C_1$–$C_6$ alkyl or $C_1$–$C_6$ alkanoyl;

$R_2$ is hydrogen, halogen, $C_1$–$C_6$ alkyl, cyano, carboxy, nitro or NHR, wherein R is hydrogen or $C_1$–$C_6$ alkyl;

$R_3$ is hydrogen or $C_1$–$C_6$ alkyl;

$R_4$ is hydrogen, hydroxy, $C_1$–$C_6$ alkoxy, $C_2$–$C_6$ alkanoyloxy, carboxy, nitro or NHR, wherein R is as defined above; and $R_5$ is hydrogen, $C_1$–$C_6$ alkyl or halogen;

wherein when Y is tetralin, quinoline, isoquinoline or indole then n is zero, 1 or 2; when Y is naphthalene, quinoline, isoquinoline or indole, then each of the substituents $OR_1$, $R_2$ and oxindolylidene may be independently on either of the aryl or heteroaryl moieties of Y, whereas only the benzene moiety is substituted when Y is tetralin; and when Y is naphthalene, tetralin, quinoline or isoquinoline, then $R_2$ is hydrogen, halogen, cyano or $C_1$–$C_6$ alkyl and $R_3$, $R_4$ and $R_5$ are hydrogen; whereas when Y is indole, then $R_2$ is hydrogen, halogen, $C_1$–$C_6$ alkyl, cyano, carboxy, nitro or —NHR, in which R is as defined above, $R_3$ is hydrogen or $C_1$–$C_6$ alkyl, $R_4$ is hydrogen, hydroxy, $C_1$–$C_6$ alkoxy, $C_2$–$C_6$ alkanoyloxy, carboxy, nitro or —NHR, wherein R is as defined above, and $R_5$ is hydrogen, halogen or $C_1$–$C_6$ alkyl; and (b) as a separate composition, an effective amount of an antitumor agent.

* * * * *